United States Patent
Lam et al.

(10) Patent No.: US 9,244,390 B2
(45) Date of Patent: Jan. 26, 2016

(54) TECHNIQUES TO DETERMINE CONCENTRATION PARAMETERS OF CONDUCTIVE LIQUID ELECTROPHORETIC (LEP) INKS

(75) Inventors: Quang P Lam, Union City, CA (US); Doris Chun, Santa Clara, CA (US); Hou T. Ng, Campbell, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 14/391,137

(22) PCT Filed: Jul. 31, 2012

(86) PCT No.: PCT/US2012/049050
§ 371 (c)(1),
(2), (4) Date: Oct. 7, 2014

(87) PCT Pub. No.: WO2014/021869
PCT Pub. Date: Feb. 6, 2014

(65) Prior Publication Data
US 2015/0071665 A1   Mar. 12, 2015

(51) Int. Cl.
G03G 15/10 (2006.01)
G03G 15/08 (2006.01)
G01N 27/02 (2006.01)
G03G 21/00 (2006.01)

(52) U.S. Cl.
CPC .............. *G03G 15/105* (2013.01); *G01N 27/02* (2013.01); *G03G 15/0851* (2013.01); *G03G 21/0011* (2013.01); *B41P 2200/21* (2013.01)

(58) Field of Classification Search
CPC . G03G 15/105; G03G 15/0851; G01N 27/02; B41P 2200/21
See application file for complete search history.

(56) References Cited

U.S. PATENT DOCUMENTS

| 6,229,971 | B1 | 5/2001 | Yamamoto |
| 6,330,406 | B1 | 12/2001 | Yamaguchi |
| 2006/0232615 | A1 | 10/2006 | Berg et al. |
| 2010/0215405 | A1 | 8/2010 | Patton et al. |
| 2011/0102003 | A1 | 5/2011 | Bhattacharyya |
| 2012/0027431 | A1 | 2/2012 | Brown et al. |

FOREIGN PATENT DOCUMENTS

| JP | 11326254 | 11/1999 |
| JP | 2005153459 | 6/2005 |
| JP | 2011048247 | 3/2011 |

*Primary Examiner* — David Bolduc
*Assistant Examiner* — Barnabas Fekete
(74) *Attorney, Agent, or Firm* — Hewlett-Packard Patent Department

(57) ABSTRACT

Techniques to determine concentration parameters of conductive liquid electrophoretic (LEP) inks are illustrated herein. In an example, a layer of conductive LEP ink is formed on a developer roller using electrostatic forces acting on the conductive LEP ink. A current is generated in response to a voltage between a measurement electrode and a developer roller. The current flows through the conductive LEP ink layer.

12 Claims, 7 Drawing Sheets

TECHNIQUES TO DETERMINE CONCENTRATION PARAMETERS OF CONDUCTIVE LIQUID ELECTROPHORETIC (LEP) INKS

BACKGROUND

A liquid electrophoretic (LEP) ink (also known as electro-ink) is a liquid ink that aims to combine advantages of electronic printing with the qualities of liquid ink. LEP inks enable digital printing by electrically controlling the location of print particles. LEP inks may be supplied as a concentrated paste that is loaded into a LEP printer (also referred to as press) in cartridges in a "clean hands" operation. Inside the press, the LEP ink is diluted with a carrier liquid (also referred to as solvent) to form a fluid mixture of carrier liquid and electrophoretic colorant particles ready for printing. Oil may be used as carrier liquid for LEP inks.

Ink concentration of a LEP ink is an important parameter that influences print quality. For example, variation of LEP ink concentration during a print run may affect print quality.

BRIEF DESCRIPTION OF THE DRAWINGS

In order that the present disclosure may be well understood, various examples will now be described with reference to the following drawings.

DETAILED DESCRIPTION

Figure 1:
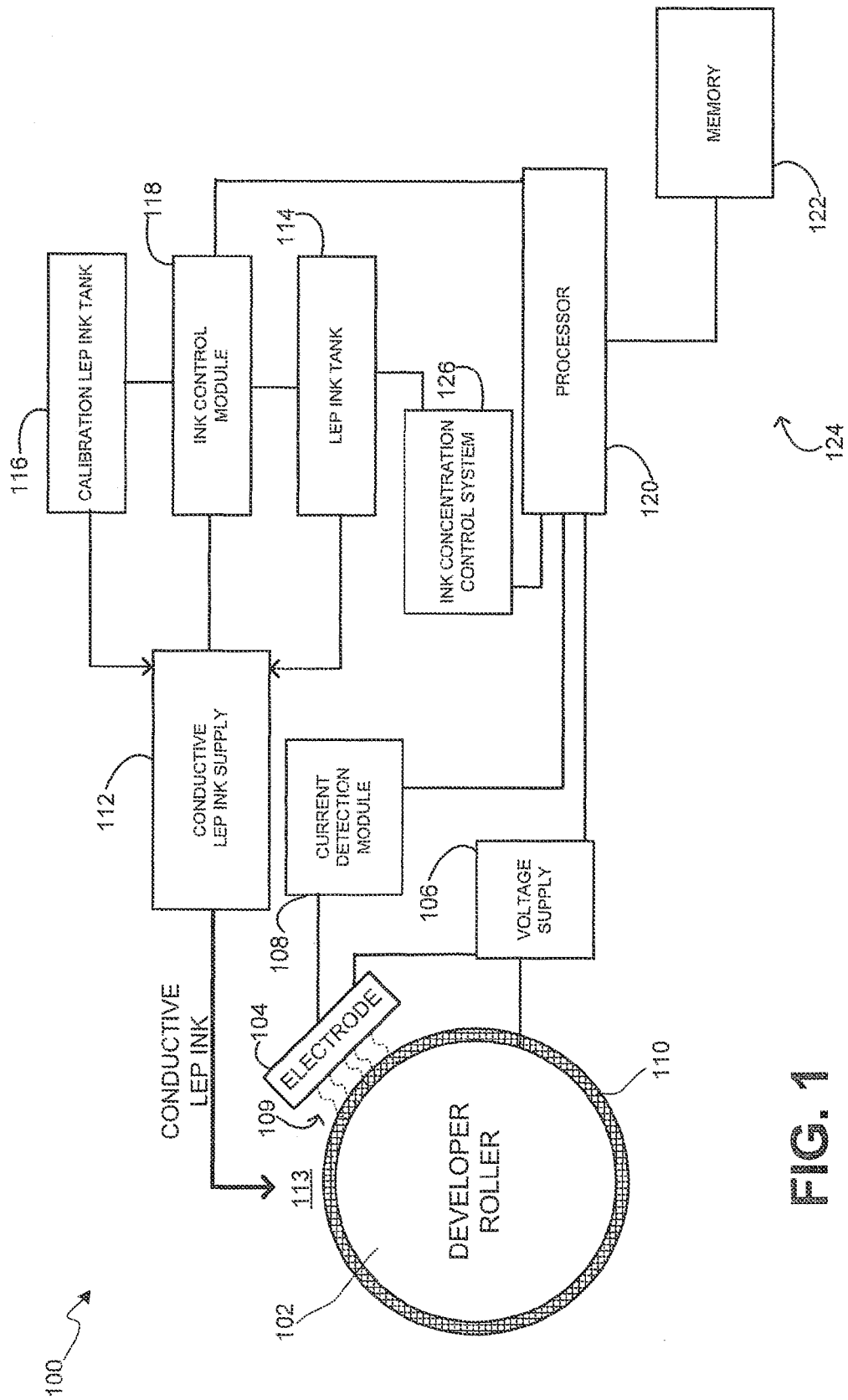
FIG. 1 is a schematic block diagram of an apparatus to determine a concentration parameter of conductive LEP inks according to examples.

In the following description, numerous details are set forth to provide an understanding of the examples disclosed herein. However, it will be understood that the examples may be practiced without these details. While a limited number of examples have been disclosed, it should be understood that there are numerous modifications and variations therefrom. While a limited number of examples are illustrated, it will be understood that there are numerous modifications and variations therefrom.

During operation of LEP printers, concentration of the LEP ink (or a related parameter) may be measured. Such measurements may be used to determine how much ink will develop and, eventually, be transferred onto the substrate. A control system may use such measurements to maintain electro-ink concentration within certain levels (variations in ink concentration may affect print quality). Further, concentration of a LEP ink outside of a LEP printed may be determined for assessing ink properties.

One manner of performing such measurement is using an optical sensor for determining optical density of a LEP ink, which is related to ink concentration. Such an optical sensor may be located in an ink tank of a LEP printer to monitor a diluted working dispersion. However, as the inventors have understood, accuracy of optical measurements on conductive LEP inks may be compromised by ink reflectivity. A conductive electro-ink includes conductive print particles. Examples of conductive LEP inks are metallic LEP inks, in which the print particles are metallic pigments such as, but not limited to, particles comprised of silver or any other metal.

Use of an ultrasound sensor has also been proposed to measure concentration of LEP inks. However, sensors using ultrasound waves face implementation challenges in a working dispersion due to air bubbles originated from agitating pumps.

Therefore, use of optical sensors or ultrasound sensors may be not convenient for some particular applications of LEP inks and, more specifically, for applications in which conductive LEP inks are used (e.g., for printing metallic colors).

As the inventors have understood, detecting a current generated in response to a voltage between a measurement electrode and the developer roller, the current flowing through a conductive LEP ink layer, may be particularly convenient to measure a concentration parameter of a conductive LEP ink. In examples, the detected current is used to determine concentration of the conductive LEP ink or to operate an LEP printer. Detecting the current generally includes determining an electrical parameter related to the current. For example, detecting the current may include measuring values of the current flowing through the conductive LEP ink layer. In other examples, detecting the current includes measuring values of a voltage drop through the conductive LEP ink layer. Apparatuses described herein may determine concentration of the conductive LEP ink, or control operation of a LEP printer, based on values of the electrical parameter. It will be understood that the above electric parameters are not limited to such current or voltage values.

Concentration parameters may be expressed in different forms. For example, a concentration parameter may be expresses as a relationship between pigment and carrier liquid (e.g. oil) in %. In another non-limiting example, a concentration parameter may be expressed as the number of pages to be printed with an initial volume of ink in a solvent. (For a fixed initial volume of ink in a solvent, there are a number of pages that can be printed with a specific quality.) For example, for determining ink concentration, a print run may be performed without modifying the ink concentration at an ink tank (e.g., ink tank 118 or 226 in FIGS. 1 to 3). The number of pages that can be printed with a pre-determined threshold quality is directly correlated to ink concentration at the beginning of the print run and can be used as concentration parameter. Further, a concentration parameter may be a parameter to be kept constant in an ink concentration loop (illustrated below with respect to FIG. 8).

FIG. 1 schematically shows a block diagram of an apparatus 100 to determine a concentration parameter of a conductive LEP ink. Apparatus 100 may form part of an LEP printer (more specific details of LEP printers are illustrated with respect to FIGS. 2 and 3). Alternatively, apparatus 100 may form part of a dedicated system to determine concentrations of conductive LEP inks.

Apparatus 100 includes a developer roller 102, a measurement electrode 104 adjacent to developer roller 102, a voltage supply 106 to apply a voltage between developer roller 102 and measurement electrode 104, and a current detection module 108 to detect a current 109 between measurement electrode 104 and developer roller 102 in response to a voltage applied by voltage supply system 106. As illustrated, current 109 is generated in response to a voltage applied between measurement electrode 104 and developer roller 102. Current 109 flows through a conductive LEP ink layer 110.

Developer roller 102 is to receive layer 110 of conductive LEP ink using electrostatic forces acting on the conductive LEP ink. More specifically, an electric field (not shown) may be generated in a region 113 contiguous to developer roller 102; charged conductive LEP ink may be provided at that region (e.g., by a conductive LEP ink supply 112); the electric field is such that the charged conductive LEP ink migrates towards the surface of developer roller 102 and, thereby, forms layer 110. More specific examples of this process are illustrated below with respect to FIGS. 2 and 3. In some examples, the electric field for forming layer 110 is generated by a so-called main electrode disposed in the proximity of developer roller 102 (e.g., electrode 310 shown in FIG. 3).

Electrode 104 may be comprised of any conductive element suitable to generate an electric field that causes a current between the measurement electrode and the developer roller. This current magnitude is co-related to concentration of the conductive LEP ink as illustrated below with regard to FIG. 5. Measurement electrode 104 is disposed adjacent to developer roller 102 such that current 109 can be generated between measurement electrode 104 and through layer 110.

Electrode 104 may be exclusively dedicated to generating current 109, i.e., the current used to measure a concentration parameter of the conductive LEP ink. In that case, an additional electrode (not shown in FIG. 1; an example being main electrode 310 in FIG. 3) may be provided to form layer 110 on developer roller 102. In other examples, electrode 104 may perform additional functions. In an example, electrode 104 may also be responsible to generate the electric field inducing formation of layer 110 on developer roller 102. More specifically, electrode 104 may be integrated in the main electrode of a binary ink developer (e.g., main electrode 310 in FIG. 3). In other examples, another functional element adjacent to developer roller 102 (e.g., a squeegee roller, or a cleaning roller of a binary ink developer) is configured to generate a current used to measure a concentration parameter of the conductive LEP ink. Further examples are illustrated below with respect to FIG. 3.

Current detection module 108 may include any circuitry and/or sensing elements suitable for detecting current 109 between measurement electrode 104 and developer roller 102. For example, current detection module 108 may be electrically connected to electrode 104 for having access to a current flowing therethrough.

According to some examples, current detection module 108 detects the current by measuring values of the current flowing through the conductive LEP ink layer. For example, current detection module 108 may include a shunt resistor to measure a voltage caused by the flowing current. Current detection module 108 may use a calibration of the shunt resistor to determine the value of the flowing current. In other examples, current detection module 108 detects the current by measuring values of a voltage drop through the conductive LEP ink layer. For example, current detection module 108 may ground developer roller 102 and measure the voltage drop across layer 110. The voltage drop may also be used to derive values of the current. Therefore, it will be understood that operation of an LEP printer and measurement of ink concentration as described herein may be performed using such current or voltage values or other suitable electrical parameters related to the current flowing through the conductive LEP ink layer.

In some examples, current detection module 108 is incorporated into a high voltage power supply electrically connected to the measurement electrode for providing an operating voltage. In such cases, current values or voltage values measurement may be provided as a digital output from the high voltage power supply. In examples where the measurement electrode 104 is part of the main electrode supplying the developing voltage, this high voltage power supply may be also responsible to supply the developing voltage.

As illustrated in FIG. 1, apparatus 100 may further include a conductive LEP ink supply 112 (hereinafter referred to as ink supply 112) to supply conductive LEP ink at a region 113 adjacent to developer roller 102. An example of an ink supply system is illustrated below with respect to FIG. 3. Ink supply 112 may be provided with conductive LEP ink from a conductive LEP ink tank 114. The ink from tank 114 may be used to form an image during operation of apparatus 100 as part of a LEP printer. Alternatively, apparatus 100 may be configured as a dedicated system for measuring ink concentration of ink from tank 114.

If apparatus 100 forms part of a LEP printer, tank 114 may be operatively connected to ink concentration control system 126 to control ink concentration in the tank. Ink concentration control system 126 may include a system of reservoirs and pumps (not shown) to controllably supply colorant particles (e.g., in the form of a concentrated paste), carrier liquid, and/or a mixture thereof into tank 114 so as to vary concentration of the ink in the tank.

As illustrated in FIG. 1, apparatus 100 may further include a calibration LEP ink tank 116 for receiving a batch of calibration conductive LEP ink. The calibration conductive LEP ink is for being provided with an LEP ink composition prepared such that concentration of the ink is known. Apparatus 100 may be operated with the LEP ink composition having a pre-determined concentration. Thereby, measurements of an electrical parameter (e.g., current values or voltage values) related to the current can be correlated to ink concentration and apparatus 100 calibrated for measuring ink concentration.

Calibration LEP ink tank 116 may be provided in addition to tank 116. An additional tank for calibration facilitates calibration of apparatus 100 for concentration measurement without interrupting operation of apparatus 100. This might be particularly convenient if apparatus 100 forms part of a printing system since, then, calibration can be performed without interrupting a print run of the printer. Alternatively, apparatus 100 can be provided with a single tank for receiving conductive LEP ink, thereby simplifying design of apparatus 100. In the latter case, calibration of apparatus 100 can be performed by introducing a batch of calibrated LEP ink.

Generally, apparatus 100 may further include an ink control module 118 for controlling operation of at least one of conductive LEP ink supply 112, LEP ink tank 114, or calibration LEP ink tank 116. More specifically, ink control module 118 may control supply of conductive LEP ink to region 113. Ink control module 118 may include fluid connections, valves, processors, as well as controllers for controlling ink supply. It will be understood that ink control module 118 may include further elements.

Apparatus 100 may further include a control system 124. Control system 124 may include a processor 120 configured to run control programs stored in memory 122 for operation of apparatus 100.

In the illustrated example, processor 120 is operatively connected to the elements mentioned above to control their operation as described herein. More specifically, processor 120 is illustrated configured to control voltage supply 106, current detection module 108, ink control module 118, and ink concentration control system 126. It will be understood that processor 120 may be configured to operate only some of these elements (e.g., supply 106 and module 108).

Elements of apparatus 100 may be controlled by another processor or may be configured to operate independently. Further, processor 120 may control additional elements in apparatus 100 not shown in the illustrated example. Alternatively as illustrated in FIG. 1, processor 120 may not form part of apparatus 100. For example, operation of apparatus 100 may be controlled by an external computing system.

It will be appreciated that control system 124 can be realized in the form of hardware, software module or a combination of hardware and the software module. Any such software module, which includes machine-readable instructions, may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are examples of a non-transitory computer-readable storage medium that are suitable for storing a program or programs that, when executed, for example by a processor, implement embodiments. Accordingly, examples provide a program comprising code for implementing a system or method and a non-transitory computer readable storage medium storing such a program.

Processor 120 and memory 122 may be configured to associate currents detected by current detection module 108 with a concentration parameter of the conductive LEP ink. More specifically, memory 122 may store look-up tables or models co-relating detected currents with values of an ink concentration parameter as well as software for implementing the current-concentration association. Such look-up tables may be built using a suitable electrical parameter related to a measurement current generated as described herein. Further, processor 120 and memory 122 may be configured to operate ink control module 118 for controlling concentration of the conductive LEP ink in the conductive LEP ink container using detected currents.

Figure 2:
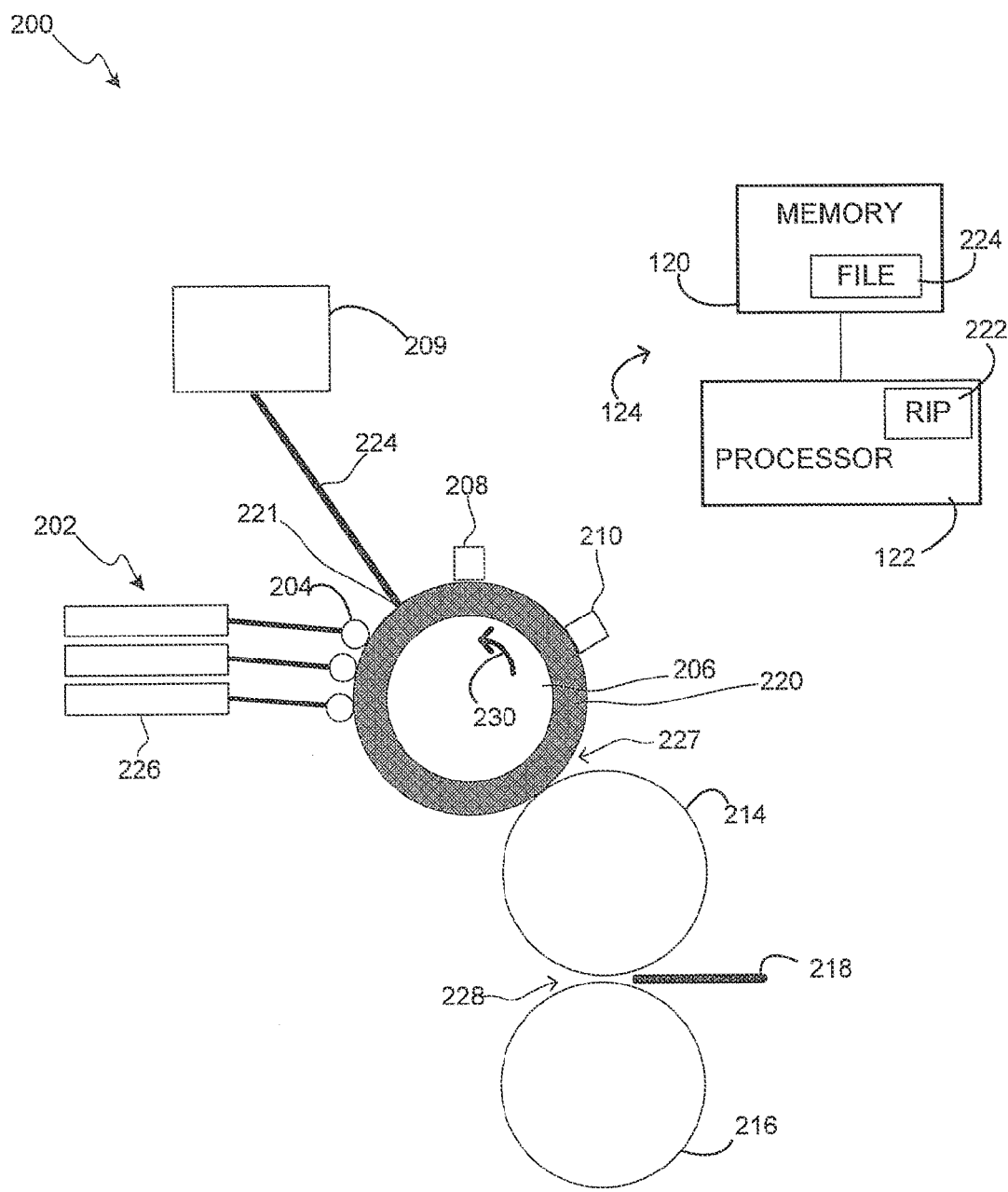
FIG. 2 is a schematic block diagram of a LEP printer according to examples.

FIG. 2 shows a schematic block diagram of a liquid electrophotographic (LEP) printer 200 according to examples herein. An LEP printer refers to a print system working under the principles of digital offset color technology. More specifically, an LEP printer refers to a printer that creates a printed image from digital data by forming an inked image on a photo imaging element using a LEP ink, transferring the inked image to a blanket element, and transferring the inked image from the blanket element to a substrate held by an impression element. It will be understood that the example of FIG. 2 is merely illustrative. There is a variety of configurations available for implementing LEP printers. Indigo Digital Printing Presses are examples of LEP printers.

LEP Printer 200 includes LEP ink suppliers 202, developers 204, an imaging cylinder 206, a charging system 208 to electrostatically charge a photo imaging plate (PIP) 220 mounted on imaging cylinder 206, an imager unit 209 to form an electrostatic image on PIP 220, a removal system 210 of residual ink and electrical charge from PIP 206, and an impression cylinder 216 to hold a substrate 218 to be printed. LEP printer 200 may include control system 124 being comprised of a processor 122 communicatively coupled to a memory 120 for controlling operation of LEP printer 200. Control system 124 may be constituted analogously as illustrated above with respect to FIG. 1.

During operation of LEP printer 200 for printing an image onto substrate 218, charging system 208 charges PIP 220. PIP 220 may be comprised of a photoconductor film attached to the surface of imaging cylinder 206. Charging system 208 may be comprised, for example, of a corona wire or a charge roller used to generate charges. More specifically, such elements of charging system 208 may be configured to generate electrical charges which flow towards the PIP surface and cover it with a uniform static charge.

As PIP 220 continues to rotate, a charged PIP section 221 passes the imaging unit 209. Imaging unit 209 may form an electrostatic image on charged PIP section 221 by scanning one or more laser beams 224 on the surface of PIP 220. When laser beam 224 exposes charged areas of PIP section 221, it dissipates (neutralizes) charge in those areas. Thereby, an electrostatic image is formed (also referred to as latent image) in the form of an electrostatic charge pattern that replicates the image to be printed. The formed electrostatic image corresponds to the image to be printed on substrate 218. Imager unit 209 may be controlled by a raster image processor (RIP) 222 implemented at control system 124. RIP 222 converts instructions from a digital file 224 into "on/off" instructions for lasers controllers (not shown) at imager unit 209.

Developers 204 may then ink a section of PIP 220 containing a portion of a latent image with charged LEP ink. At least one of developers 204 is to supply the PIP section with conductive LEP ink. A more specific example of a developer and, more specifically, a binary ink developer (BID) is illustrated below with respect to FIG. 3. It will be understood that there is a number of alternatives for constituting developers 204 not limited to the examples specifically mentioned herein.

The charged LEP ink coats the surface of PIP 220 according to the formed electrostatic image so as to form an ink image thereon. Generally, there is a developer for each basic color available to LEP printer 200. FIG. 2 shows three developers 204 for the sake of illustration. It will be understood that LEP printer 200 may include any number of developers suitable for a specific application. The basic colors correspond to LEP inks to be supplied by tanks 226. These basic colors define the color gamut of LEP printer 200. According to examples herein, at least one of tanks 226 is to supply a conductive LEP ink. Further, according to at least examples herein, at least one of tanks 226 may be to supply a calibrated LEP ink as illustrated above with respect to FIG. 1.

The surfaces of PIP 220 and blanket cylinder 214 contact at a transfer area 227. Thereby, the ink image formed on the surface of PIP 220 may be transferred to the surface of blanket cylinder 214.

A heating system (not shown) may heat the inked image carried by blanket cylinder 214. For example, blanket cylinder 214 may be heated to approximately 100° C. to cause pigment carrying particles of the LEP ink to melt and blend into a smooth liquid plastic before reaching a further transfer area 228, in which the surface of blanket cylinder 214 contacts substrate 218 held by impression cylinder 216. When the heated LEP ink on blanket cylinder 214 contacts the cooler substrate 218, the LEP ink solidifies, adheres, and transfers to substrate 218. Print finishing can be performed immediately.

Removal system 210 may remove any residual ink and/or electrical charge on PIP 220 so that a new ink image can be formed thereon. More specifically, downstream transfer area 227, removal system 210 may (i) remove excess liquids and ink particles from the non-image areas on the surface of PIP 220, and (ii) cool the surface of PIP 220. For example, two small rollers (wetting roller and reverse roller, not shown) may be configured to rotate opposite to direction 230, i.e. the rotation direction of PIP 220. The reverse roller may be mounted in close proximity to the surface of PIP 220. Thereby, it may exert a combination of electrodynamic and hydrodynamic forces that remove excess liquids and ink particles from the PIP surface. Ink removed from the PIP at this stage may be recovered in a catch tray (not shown) and sent to a separator (not shown).

The above described operation of LEP printer 200 may be repeated for every color separation in the image.

Figure 3:
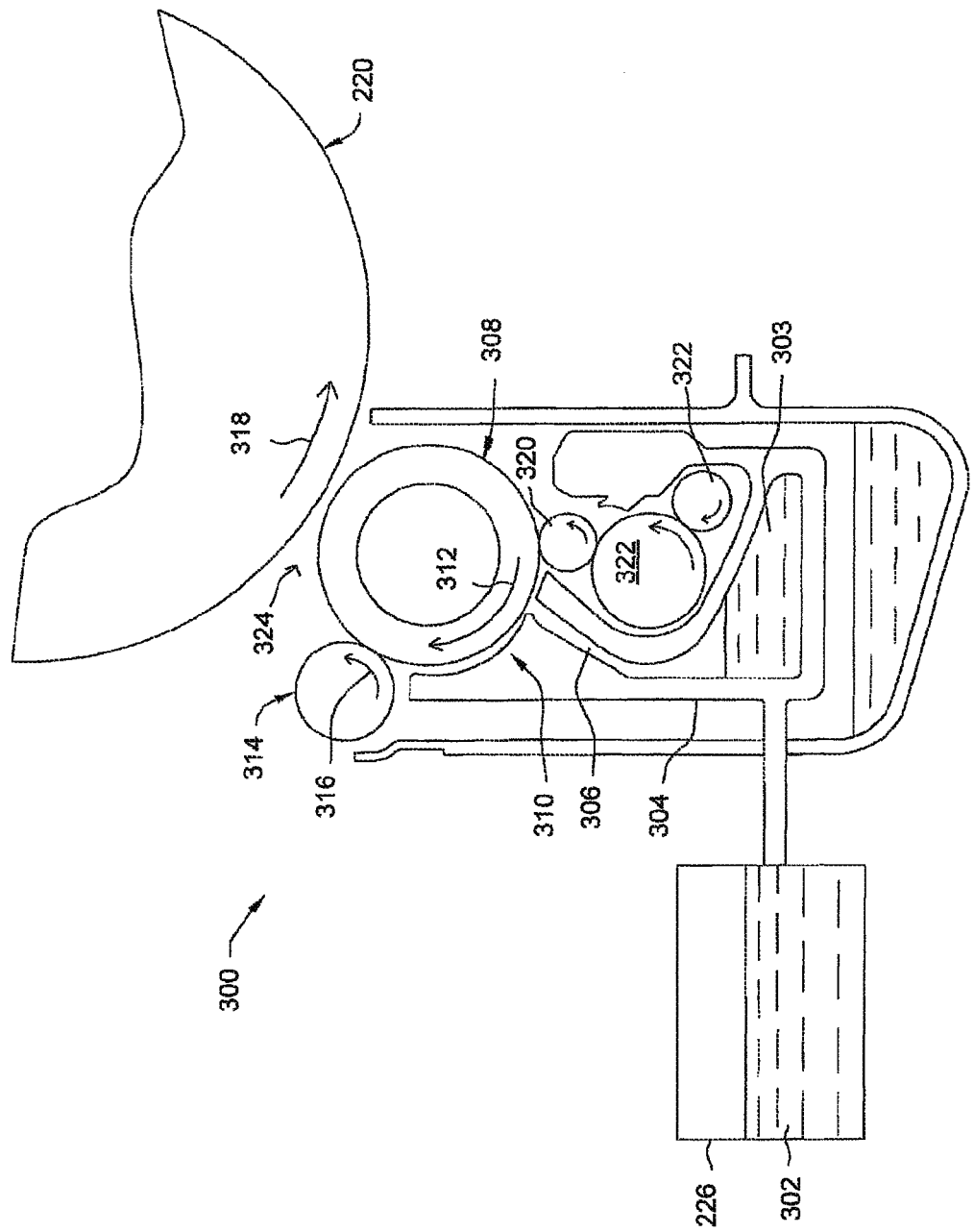
FIG. 3 is a partial cut-away view of a binary ink developer of a LEP printer according to examples.

FIG. 3 is a partial cut-away view of a binary ink developer (BID) 300 of a printing system of a liquid electro-photographic printer (e.g., LEP printer 200 illustrated above with respect to FIG. 2) according to examples. BID 300 is associated to PIP 220, which may be constituted as described above with respect to FIG. 2. BID 300 may constitute at least one of developers 204 of LEP printer 200.

A tank 226 is connected to BID 300. Conductive LEP Ink 302 in tank 226 may be transported to BID 300 as described in greater detail below. Generally, ink 302 in tank 226 is electrically neutral. As described in greater detail below, Conductive LEP Ink 302 contains particles that may be charged so as to charge the ink during the printing process. Tank 226 may be operatively connected to an ink concentration control system (e.g., ink concentration control system 126 illustrated above with respect to FIG. 1) to vary concentration of conductive LEP ink 302 in tank 302.

BID 300 may further include a reservoir 304 that stores ink 303. Ink 303 may be pumped to reservoir 304 from tank 226. A channel 306 extending from reservoir 304 enables ink 303 to flow to a developer roller 308. Ink from developer roller 308 transfers to PIP 220 by way of electrostatic forces.

More specifically, developer roller 308 includes a main electrode 310 associated therewith that serve to electrically charge ink 303. Main electrode 302 is sometimes referred as the first electrode. A development voltage is applied between main electrode 302 and developer roller 308 to generate an electric current to charge ink 303. Thereby, in response to the electric current, an ink development layer can be formed onto developer roller 308. This ink development layer is, generally, a function of the development voltage applied by the main electrode 310 relative to developer roller 308. The ink development layer is to be transferred onto PIP 220 at a transfer region 324 according to an electrostatic latent image formed on PIP 220 as illustrated above with respect to FIG. 2.

Developer roller 308 rotates in a direction 312 as viewed from FIG. 3. As described in greater detail below, the rotation of the developer roller 308 and the electric field applied between developer roller 308 and main electrode 310 enable ink 303 charged by main electrode 310 to be applied to developer roller 308. In addition, the rotation enables ink to be removed from developer roller 312 and applied to PIP 220 as described in greater detail below.

Main electrode 310 may also be used to generate a current, which magnitude is indicative of concentration of ink 303. In examples, main electrode 310 may implement the functionality of measurement electrode 104, illustrated above with respect to FIG. 1. For implementing such examples, measurements of the first current may be used to measure a concentration parameter of ink 302. More specifically, voltage supply 106 (shown in FIG. 1) may be electrically connected to main electrode 302 for generating a voltage between main electrode 302 and developer roller 308. Such voltage may generate a current through ink on a section of developer roller 308. That current is co-related with the concentration of the conductive LEP ink as further illustrated below with regard to FIGS. 5 and 6. Current detection module 108 may be electrically connected to main electrode 302 to facilitate measurement of an electrical parameter related to the current (e.g., values of current or voltage drop).

BID 300 further includes a squeegee electrode 314. Squeegee electrode 314 is configured as a roller that, in operation, rotates in a direction 316 as viewed from FIG. 3. Direction 316 is opposite direction 312 (rotation direction of developer roller 308). A voltage may be applied between squeegee electrode 314 and developer roller 308. For example, squeegee electrode 314 may be electrically connected to a voltage supply (e.g., voltage supply 106, depicted in FIG. 1). The rotation of squeegee electrode 314 and the voltage applied to the squeegee electrode 314 facilitates further charging ink on a section of developer roller 308 passing under the squeegee electrode 314.

Squeegee electrode 314 may also be used to generate a current, which magnitude is indicative of concentration of ink 303. More specifically, squeegee electrode 314 may also implement the functionality of measurement electrode 104, namely, generating a current to be used for measuring a concentration parameter of ink. For example, voltage supply 106 (shown in FIG. 1) may be electrically connected to squeegee electrode 314 for generating a voltage between squeegee electrode 314 and developer roller 308. Such voltage may generate a current through ink on a section of developer roller 308. That current is co-related with the concentration of the conductive LEP ink as further illustrated below with regard to FIGS. 5 and 6. This current may be the same as the one used for further charging ink on developer roller 308. Current detection module 108 may be electrically connected to squeegee electrode 314 to facilitate measuring the current.

In some examples, BID 300 may further include a cleaner roller 320 adjacent to developer roller 308 at a region downstream (relative to the rotation direction 312 of developer roller 308) of ink transfer region 324. Cleaner roller 320 is to clean any excess ink remaining on a section developer roller 308 after transferring ink from that section onto PIP 220. Cleaner roller 320 may collaborate with further rollers 322 for conveying excess ink back to reservoir 304. Thereby, excess ink may be re-utilized for forming further ink development layers onto development roller 308.

Cleaner roller 320 may also be used to generate a current, which magnitude is indicative of concentration of ink 303. More specifically, cleaner roller 320 may implement the functionality of measurement electrode 104, namely, generating a current to be used for measuring a concentration parameter of ink. For example, voltage supply 106 (shown in FIG. 1) may be electrically connected to cleaner roller 320 for generating a voltage between cleaner roller 320 and developer roller 308. Such voltage may generate a current through ink on a section of developer roller 308. That current is co-related with the concentration of the conductive LEP ink as further illustrated below with regard to FIGS. 5 and 6. Current detection module 108 may be electrically connected to cleaner roller 320 to facilitate measuring the current.

In some examples, BID 300 may include a further electrode (not shown) in addition to main electrode 310, squeegee electrode 314, cleaner roller 320 to implement the functionality of measurement electrode 104. In such examples, the further electrode is dedicated to generate a current to be used for measuring a concentration parameter of ink.

Figure 4:
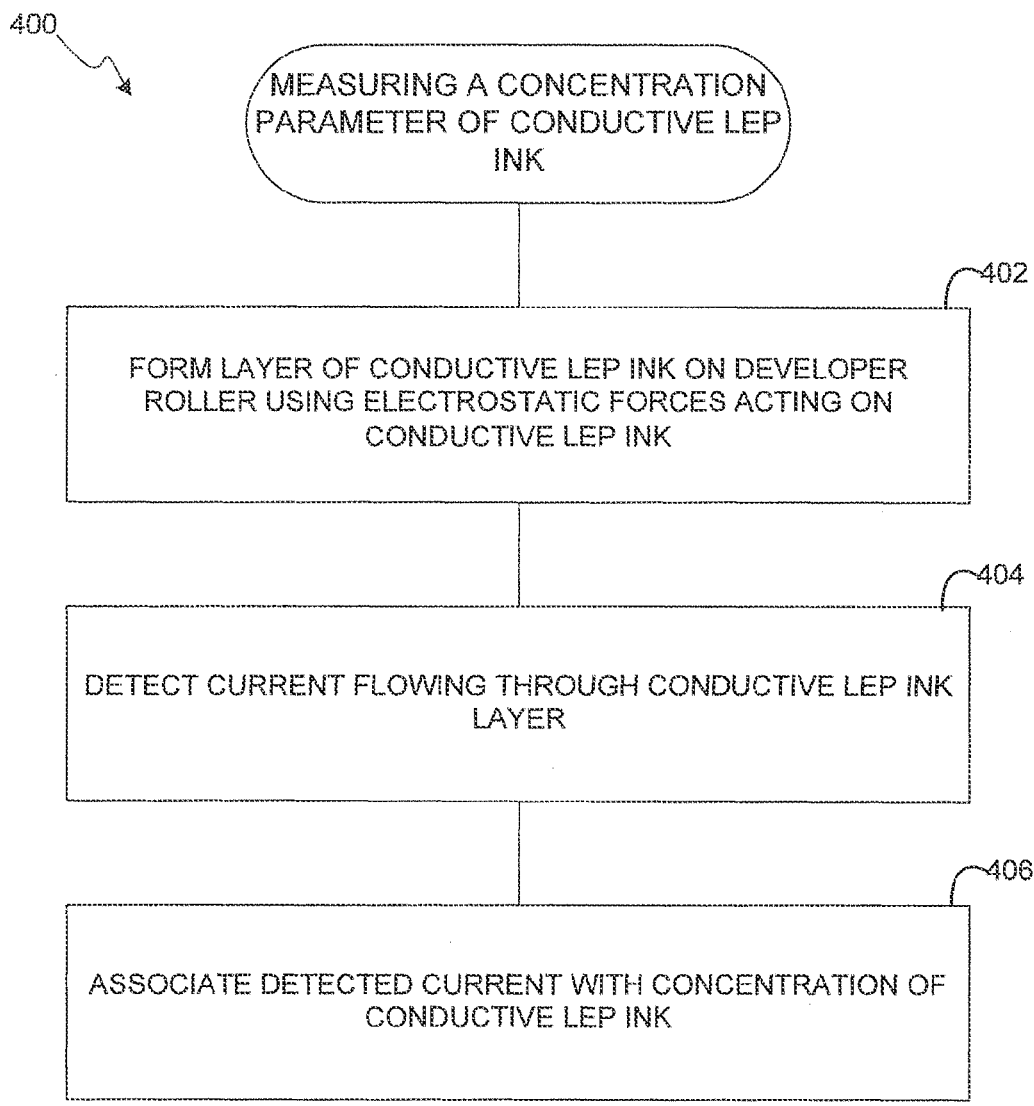
FIG. 4 shows a process diagram illustrating examples of methods to measure a concentration parameter of conductive LEP inks.

FIG. 4 shows a process diagram 400 illustrating examples of methods to measure a concentration parameter of a conductive LEP ink. In discussing FIG. 4, reference is made to FIGS. 1 to 3 to provide contextual examples. Implementation, however, is not limited to those examples.

At block 402, a layer of conductive LEP ink is formed on a developer roller using electrostatic forces acting on the conductive LEP ink. Main electrode 310, shown in FIG. 2, may be responsible for implementing this block by generating an electric current that charges conductive LEP ink and induces formation of the a layer of the conductive LEP ink on a developer roller using electrostatic forces acting on the conductive LEP ink onto developer roller 312.

At block 404, a current flowing through the conductive LEP ink layer is detected. The current is generated in response to a voltage between a measurement electrode and the developer roller. Further, the current flows through the conductive LEP ink layer. Examples of such measurement electrodes are illustrated above with respect to FIGS. 1 to 3. More specifically, main electrode 310, squeegee electrode 314, a cleaner roller 320, or an additional electrode may be used to implement the measurement electrode. As illustrated with respect to FIGS. 5 and 6, the detected current is co-related with the concentration of the conductive LEP ink. Detecting the current at block 404 generally implies measurement of an electrical parameter related to the current. For example, but not limited thereto, such electrical parameter may include measuring values of the current flowing through the conductive LEP ink layer or values of a voltage drop through the conductive LEP ink layer.

Figure 5:
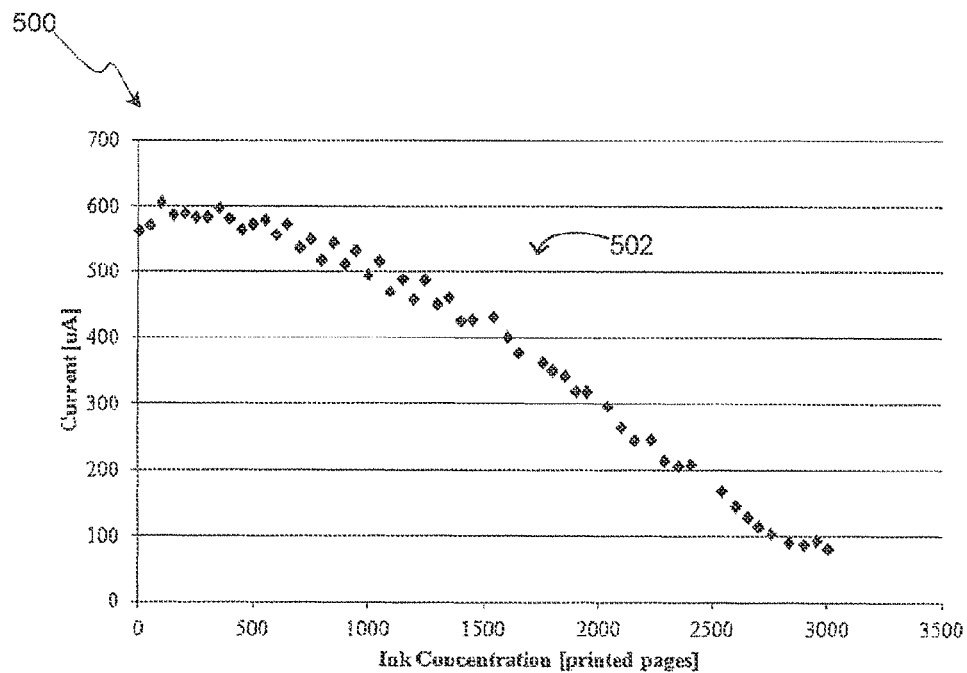
FIG. 5 shows an example graph illustrating behavior of conductive LEP inks.

FIG. 5 shows a graph 500 illustrating behavior of a conductive LEP ink in response to a current flowing between a measurement electrode and the developer roller and through the LEP ink layer. More specifically, graph 500 includes measurement data 502 of the current versus ink concentration. (In this particular example, the ink concentration parameter is printed pages with a specific volume of ink.) As can be appreciated, measurement data 502 co-relates the current and an ink concentration parameter since a steady variation of measurement data 502 can be determined.

Figure 6:
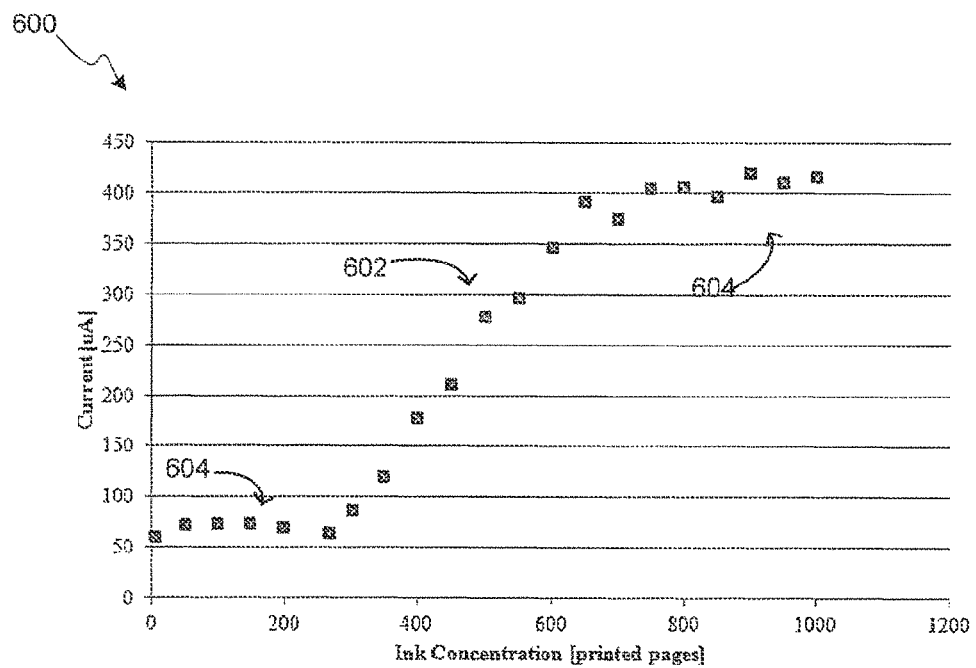
FIG. 6 shows an example graph illustrating behavior of non-conductive LEP inks.

It is worth noting, that the co-relation between current and ink concentration illustrated in FIG. 5 seems not to apply to non-conductive LEP inks, as illustrated in FIG. 6. FIG. 6 shows a graph 600 illustrating behavior of a non-conductive LEP ink in response to a current flowing between a measurement electrode and the developer roller and through the LEP ink layer. More specifically, graph 600 includes measurement data 602 of the current versus ink concentration. As can be appreciated, measurement data 602 does not co-relate the current and an ink concentration parameter over the illustrated range since steady variation of measurement data 602 cannot be determined due to the presence of plateaus 604. In other words, the range at which there is a steady variation of current for a non-conductive ink is rather narrow. Generally, this range is outside the operating parameters of the LEP printer. The inventors' present hypothesis is that non-conductive LEP ink has a relatively low maximum size of the ink development layer due to screening effect of charged particles irrespective of ink solids concentration. However, it appears that this screening effect of charged particles does not affect conductive LEP inks. Therefore, the current generated using a measurement electrode as described herein can be conveniently used to measure a concentration parameter as described herein.

Referring back to FIG. 4, at block 406 the detected current is associated with the concentration parameter of the conductive LEP ink. Control system 124 and, more specifically, processor 120 in association with memory 122 (shown in FIG. 1), may be responsible to implement block 406. Block 406 generally includes associating the current measurement electrical parameter mentioned above (e.g. current values or voltage drop values) with the concentration parameter of the conductive LEP ink. For example, graph 500 in FIG. 5 may be used for pre-determining the current-concentration association to be used during execution of process diagram 400. A similar graph based on voltage drop across the ink layer may also be used for the current-concentration association.

In some examples, associating the detected current with the concentration parameter of the conductive LEP ink at block 406 may include comparing the detected current with pre-determined data relating current and conductive LEP ink concentration. More specifically, the pre-determined data may be built in a look-up table associating current or voltage drop and concentration values. In such examples, comparing the detected current with pre-determined data may be performed using such a look-up table. Alternatively, or in addition thereto, the pre-determined data may be built in a model. More specifically, the model may be derived from the pre-determined data to develop a mathematical relationship between detected current and values of the concentration parameter. Thereby, associating the determined current with the concentration parameter of the conductive LEP ink at block 406 may be implemented by comparing determined values of an electrical parameter related to the current with a pre-determined calibration curve based on the model. In some examples, the model is constituted by a polynomial fit derived from data as illustrated in FIG. 5. It will be understood that there are further methods to pre-determine the association between current and concentration.

Figure 7:
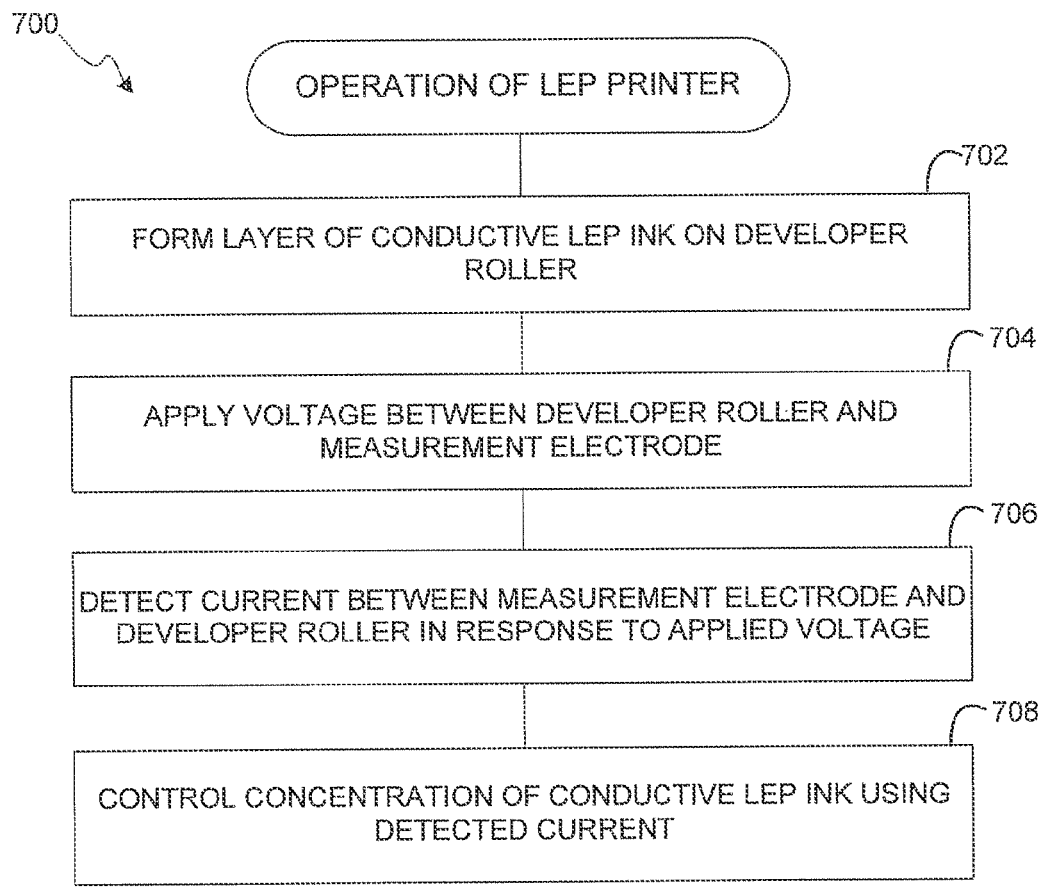
FIG. 7 shows a process diagram illustrating examples of methods to operate LEP printers.

FIG. 7 shows a process diagram 700 illustrating examples of methods to operate an LEP printer (e.g., LEP printer 200 illustrated above with respect to FIG. 2). More specifically, process diagram 700 illustrates a process that strives to maintain ink concentration constant or, at least, within a certain range during operation of a LEP printer. In discussing FIG. 7, reference is made to FIGS. 1 to 3 to provide contextual examples. Implementation, however, is not limited to those examples.

At block 702, a layer of conductive LEP ink (e.g., layer 110 shown in FIG. 1) is formed on a developer roller (e.g., developer roller 102 or 308 shown, respectively, in FIGS. 1 and 3). Block 702 may be implemented similarly as block 402 illustrated above with respect to FIG. 4.

At block 704, a voltage is applied between the developer roller and a measurement electrode. The measurement electrode may be constituted, for example, as measurement electrode 104 in FIG. 1, or as any of main electrode 310, squeegee electrode 314, cleaner roller 322 (depicted in FIG. 3) or an additional electrode in the BID. Voltage supply 106, depicted in FIG. 1, may be used for applying the voltage.

At block 706, a current is detected, the current flowing between the measurement and developer roller in response to the applied voltage. Current detection module 108 (shown in FIG. 1) may be responsible to implement block 706. The detected current is indicative of ink concentration. That is, the current may reflect a behavior of conductive LEP ink as described above with respect to FIG. 5.

At block 708, the concentration of the conductive LEP ink is controlled using the detected current. Control system 124, in cooperation with ink concentration control system 126 depicted in FIG. 1, may be responsible for implementing block 708. More specifically, memory 122 may store a set of control routines (e.g., based on the control loop illustrated with respect to FIG. 8) to be executed by processor 120 during operation of apparatus 100 as a LEP printer. For control of ink concentration, processor 120 may operate pumps at ink concentration control system 126 in order to vary ink concentration in LEP ink tank 114.

Figure 8:
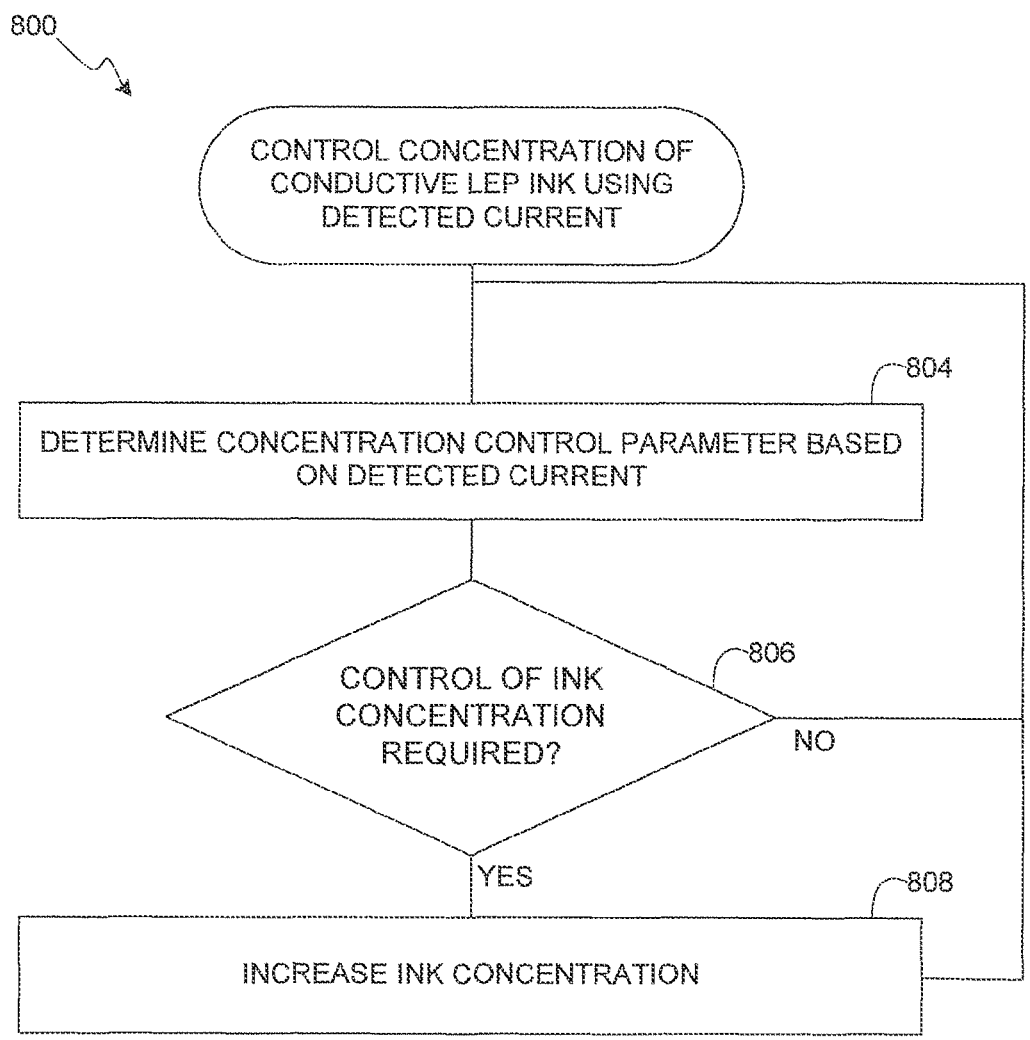
FIG. 8 shows a process diagram illustrating examples of methods to control concentration of conductive LEP inks.

FIG. 8 shows process diagram 800 illustrating methods to control concentration of the conductive LEP ink according to examples herein. It will be understood that process diagram 800 is merely illustrative and that there are a variety of methods to control concentration of conductive LEP inks based on detected currents. For example, process diagram 800 is based on a closed-loop control schema. In alternative methods, the control may be based on an open-loop schema in which, for example, detected current values are used to calculate ink concentration values and define whether and how concentration of the ink is to be modified.

At block 804, a concentration control parameter is determined based on the detected current. The specific concentration control parameter depends on the specific control loop to be implemented. In some examples, the specific concentration control parameter may correspond to ink concentration, which can be obtained as described above with respect to FIGS. 4 and 5. In some other examples, the specific concentration control parameter may correspond to raw current values or values of other related electrical parameters (e.g., voltage drop). In other words, for implementing the control loop, it is not strictly necessary to determine actual values of ink concentration.

At block 806, it is determined whether control of ink concentration is required. For example, it may be determined whether the value of the concentration control parameter is smaller than a pre-selected threshold value. If the determination is positive, control of ink concentration may be required to assure that a decrease of ink concentration affects print quality. Instead of performing the determination at block 806 using ink concentration values and ink concentration threshold values, raw values of detected current and threshold values of detected current may be used. Alternatively, raw values of other related electrical parameters, such as the voltage drop mentioned above, may be used.

If at block 806, it is determined that control of ink concentration is required (e.g., ink concentration is below a certain level), then at block 808 ink concentration is increased. For example, control system 124 may operate ink concentration control system (e.g., driving supply pumps) to add concentrated paste of LEP ink into LEP tank 114 so that the ink concentration of LEP ink tank 114 is increased. The amount of the supplied concentrated paste of LEP ink may be determined depending on a difference of the ink concentration and the pre-selected threshold value.

After block 808, process diagram 800 may go back to step 804. Also, if at block 806, it is determined that control of ink concentration is not required (e.g., ink concentration is within a certain range), then process diagram 800 may go back to step 804. Thereby, process diagram may be executed at selected time intervals for facilitating operation of an LEP printer.

In the foregoing description, numerous details are set forth to provide an understanding of the examples disclosed herein. However, it will be understood that the examples may be practiced without these details. While a limited number of examples have been disclosed, numerous modifications and variations therefrom are contemplated. It is intended that the appended claims cover such modifications and variations. Claims reciting "a" or "an" with respect to a particular element contemplate incorporation of one or more such elements, neither requiring nor excluding two or more such elements. Further, the terms "include" and "comprise" are used as open-ended transitions.

What is claimed is:

1. A method to measure a concentration parameter of a conductive liquid electrophoretic (LEP) ink, the method comprising:
    forming a layer of the conductive LEP ink on a developer roller using electrostatic forces acting on the conductive LEP ink;
    determining an electrical parameter related to a current generated in response to a voltage between a measurement electrode and the developer roller wherein the measurement electrode is comprised in a squeegee roller or a cleaning roller and wherein the measurement electrode cooperates with the developer roller in a binary ink developer, the current flowing through the conductive LEP ink layer, the current magnitude being co-related with the concentration of the conductive LEP ink; and
    associating the determined electrical parameter with the concentration parameter of the conductive LEP ink.

2. The method of claim 1, wherein associating the electrical parameter with the concentration parameter of the conductive LEP ink includes comparing the determined electrical parameter with pre-determined data relating current and conductive LEP ink concentration.

3. The method of claim 1, the method being performed during operation of an LEP printer as part of a process for controlling ink concentration.

4. The method of claim 1, wherein the method is performed during operation of an apparatus dedicated to measure conductive LEP ink concentration.

5. The method of claim 1, wherein the electric parameter correspond to values of the current flowing through the conductive LEP ink layer or to values of a voltage drop through the conductive LEP ink layer.

6. An apparatus to determine concentration parameter of a conductive LEP ink, the apparatus including,
    a developer roller to receive a layer of conductive LEP ink, the layer being formed on the developer roller using electrostatic forces;
    a measurement electrode adjacent to the developer roller;
    a binary ink developer including a squeegee roller and a cleaning roller to cooperate with the developer roller, wherein the measurement electrode forms part of the squeegee roller or the cleaning roller;
    a voltage supply to apply a voltage between the developer roller and the measurement electrode in a manner such that a current flows through the conductive LEP ink layer in response to the applied voltage;
    a current detection module to detect the current, whereby the concentration of the conductive LEP ink can be determined based on the detected current.

7. The apparatus of claim 6, wherein the apparatus forms part of a dedicated system to determine a concentration of conductive LEP inks.

8. The apparatus of claim 6, wherein the apparatus forms part of a liquid electro-photographic printer.

9. The apparatus of claim 6, wherein the current detection module detects the current by measuring values of the current flowing through the conductive LEP ink layer or values of a voltage drop through the conductive LEP ink layer and the apparatus determines concentration of the conductive LEP ink based on the current values or the voltage values.

10. A liquid electro-photographic printer to print a pattern on a substrate using a conductive LEP ink, the printer including:
    a developer roller to receive a layer of conductive LEP ink during operation of the printer, the layer being formed on the developer roller using electrostatic forces;
    a measurement electrode adjacent to the developer roller;
    a binary ink developer including a squeegee roller and a cleaning roller to cooperate with the developer roller, wherein the measurement electrode forms a part of the squeegee roller or the cleaning roller;
a voltage supply to apply a voltage between the developer roller and the measurement electrode in a manner such that a current flows through the conductive LEP ink layer in response to the applied voltage;
a current detection module to detect the current; and
an ink control module to control concentration of the conductive LEP ink using the detected current.

11. The printer of claim 10, wherein the ink control module is further to determine concentration of the conductive LEP ink based on the detected current.

12. The printer of claim 10, further including a calibration LEP ink tank to contain a conductive LEP ink dispersion at a selected concentration.

* * * * *